(12) United States Patent
Morita et al.

(10) Patent No.: US 7,753,893 B2
(45) Date of Patent: Jul. 13, 2010

(54) DRUG SOLUTION INJECTOR WITH WEIGHING SCALE

(75) Inventors: Yasuhiko Morita, Osaka (JP); Atsushi Funayama, Osaka (JP); Satoki Hino, Osaka (JP)

(73) Assignee: Nipro Corporation, Osaka (JP)

( * ) Notice: Subject to any disclaimer, the term of this patent is extended or adjusted under 35 U.S.C. 154(b) by 1007 days.

(21) Appl. No.: 10/588,962

(22) PCT Filed: Feb. 8, 2005

(86) PCT No.: PCT/JP2005/001812

§ 371 (c)(1),
(2), (4) Date: Aug. 10, 2006

(87) PCT Pub. No.: WO2005/077437

PCT Pub. Date: Aug. 25, 2005

(65) Prior Publication Data

US 2007/0173778 A1    Jul. 26, 2007

(30) Foreign Application Priority Data

Feb. 12, 2004 (JP) .............................. 2004-035198

(51) Int. Cl.
*A61M 5/00* (2006.01)
(52) U.S. Cl. ...................... 604/260; 604/246
(58) Field of Classification Search ............... 604/131, 604/132, 260, 246, 318; 128/DIG. 13; 4/144.1–144.4
See application file for complete search history.

(56) References Cited

U.S. PATENT DOCUMENTS 4,137,915 A * 2/1979 Kamen ...................... 604/65
4,722,732 A * 2/1988 Martin ...................... 604/132

FOREIGN PATENT DOCUMENTS

| JP | 61-32932 U | 2/1986 |
| JP | 03-140163 A | 6/1991 |
| JP | 5-115542 A | 5/1993 |
| JP | 06-154320 A | 6/1994 |
| JP | 07-116250 A | 5/1995 |
| JP | 11-9689 A | 1/1999 |

* cited by examiner

*Primary Examiner*—Nicholas D Lucchesi
*Assistant Examiner*—Laura A Bouchelle
(74) *Attorney, Agent, or Firm*—Birch, Stewart, Kolasch & Birch, LLP

(57) ABSTRACT

A drug solution injector for determining an accurate injection volume of a drug solution by weighing the drug solution reservoir with a weighing scale. A drug solution injector is provided with a weighing scale that is compact, does not disturb handling and enables an accurate determination of the injection volume of the drug solution. A drug solution injector includes a drug solution reservoir composed of a chamber for reserving a drug solution therein and pressurization mechanism for pushing out of the reserved drug solution. An injection line is connected to the reservoir to inject the drug solution to the body. The drug solution reservoir is fixedly provided with a weighing scale for measuring a weight of the drug solution stored in the drug solution reservoir.

12 Claims, 4 Drawing Sheets

DRUG SOLUTION INJECTOR WITH WEIGHING SCALE

TECHNICAL FIELD

The present invention relates to a drug solution injector for continually injecting a drug solution such as an anesthetic, an analgesic, an anticancer agent, an antibiotic or the like into the body.

BACKGROUND ART

Among drug solution injectors for continually injecting drug solutions such as such as an anesthetic, an analgesic, an anticancer agent, an antibiotic or the like into the body, drug solution injectors of a type that requires no power supply have widely been used in a home-care setting or in an ambulatory setting because of their high portability to administer an anticancer agent or a pain relief.

The drug solution injectors of such a type generally comprises a drug solution reservoir having a chamber for storing a drug solution therein and a pressurization mechanism for continually discharging the drug solution in the chamber to the outside, and an injection line connected to the drug solution reservoir to inject the drug solution into the body. An example of the drug solution reservoir widely used includes balloons of an elastic material. The balloons used as a drug solution reservoir is filled with a drug solution and then allowed to use contraction stress of the inflated balloon to discharge the drug solution to the outside.

The drug solution injector with such a balloon as a drug solution reservoir is generally provided with a housing for holding a balloon to protect the balloon. It has been known to mark scales corresponding to inflation and deflation of the balloon on the housing (cf. FIG. 1, scale 111). The scales make it possible to give an approximate injection volume of the drug solution (a decreased volume of the drug solution in the balloon) or an injection rate of the drug solution (cf. Patent documents 1-4). However, the above scale has been marked to give an index of the injection volume of the drug solution, thus making it difficult to determine an accurate injection volume of the drug solution because of deviations in inflated shape of the balloons at the time of balloon molding.

Patent document 1: JP H03-140163A
Patent document 2: JP H05-115542A
Patent document 3: JP H06-154320A
Patent document 4: JP H07-116250A

DISCLOSURE OF INVENTION

Problems to be Solved by Invention

In such a case, it would be possible to determine an accurate injection volume of the drug solution by weighing the drug solution reservoir with a weighing scale such as an electronic balance. However, this procedure is difficult to achieve at home and is inconvenient even in hospitals since it requires use of the weighing scale at each measurement.

It is an object of the present invention to provide a drug solution injector that enables to solve problems mentioned above, is compact, does not disturb handling and enables to determine an accurate injection volume of the drug solution with simple procedure.

Means for Solving the Problems

The present invention has been achieved by the finding that the above problems are solved by incorporating a simple weighing scale for weighing a drug solution in a drug solution reservoir into a drug solution injector for continually injecting of a drug solution such as an anesthetic, an analgesic agent, an anticancer agent, an antibiotic, etc. into the body.

More specifically, the present invention relates to:

(1) a drug solution injector comprising a drug solution reservoir having a chamber for storing a drug solution therein and a pressurization mechanism for continually discharging the drug solution in the chamber to the outside; and an injection line connected to the drug solution reservoir to inject the drug solution into the body, said drug solution injector being characterized in that said drug solution reservoir is fixedly provided with a weighing scale for measuring a weight of the drug solution stored in the drug solution reservoir.

(2) The drug solution injector described in the above section (1), wherein the drug solution reservoir is a balloon composed of an elastic material.

(3) The drug solution injector described in the above section (1), wherein the weighing scale comprises an elastic body fixed at one end thereof to the drug solution reservoir and is the one that measures the displacement of the elastic body to determine the weight of the drug solution contained in the drug solution reservoir.

(4) The drug solution injector described in the above section (3), wherein the elastic body is extensible in the direction substantially parallel to the axial direction of the injection line.

(5) The drug solution injector described in the above section (3), wherein the elastic body is a coil spring and wherein the coil spring is arranged so that the injection line passes through the coil of the spring, the spring being fixed at one end thereof to the drug solution reservoir or injection line, said injection line being marked with graduations or scales in the axial direction of the injection line to determine a length of expansion and contraction of the spring.

(6) The drug solution injector described in the above section (3), wherein the elastic body is provided with a holding portion on the other end opposite to one end fixed to the drug solution reservoir.

(7) The drug solution injector described in the above section (1), which further comprises a housing for protecting the drug solution reservoir.

EFFECT OF INVENTION

The drug solution injector according to the present invention is provided with a weighing scale, thus making it possible to determine a volume of the drug solution charged in the drug solution reservoir with ease and accuracy without need for any specific equipment, which in turn makes it possible to get an injection volume and injection rate of the drug solution during injection of the drug solution. This will enable the user to sense and take prompt action on any troubles including improper administration of the drug solution caused by errors in the preparatory stages of the drug solution injector such as at the time of filling of the drug solution or failure in the drug solution injector.

According to the present invention, the drug solution injector can be made into compact as a whole by use of an elastic body in the weighing scale. In particular, when the elastic body is so arranged as to be expandable in the direction parallel to the axial direction of the injection line, it is possible to fill the reservoir with the drug solution without being disturbed by the weighing scale. Further, there is almost no disturbance in the measurement of weight since the elastic body extends in the same direction as the elongated injection line. It is possible to provide a more compact drug solution injector in case that the elastic body is a coil spring and is so arranged that the injection line passes through an interior of the coil spring.

Further, the weighing scale can be constructed by providing a scale on the injection line and fixing the elastic body such as a spring or rubber member so that it is expandable in the axial direction of the injection line. Thus, it is possible to decrease in the number of the drug solution injector components, which is in turn effective for reduction in cost of the drug solution injector. In case of the drug solution injector with such a construction, the measurement of weight can be carried out with a simple method that involves steps of picking up the drug solution injector with the injection line being extended upward, holding the holding portion fixed to one end of the elastic body with fingers, releasing the hand from the injection line and reading the scale character on the injection line.

DESCRIPTION OF REFERENCE SYMBOLS

Figure 1:
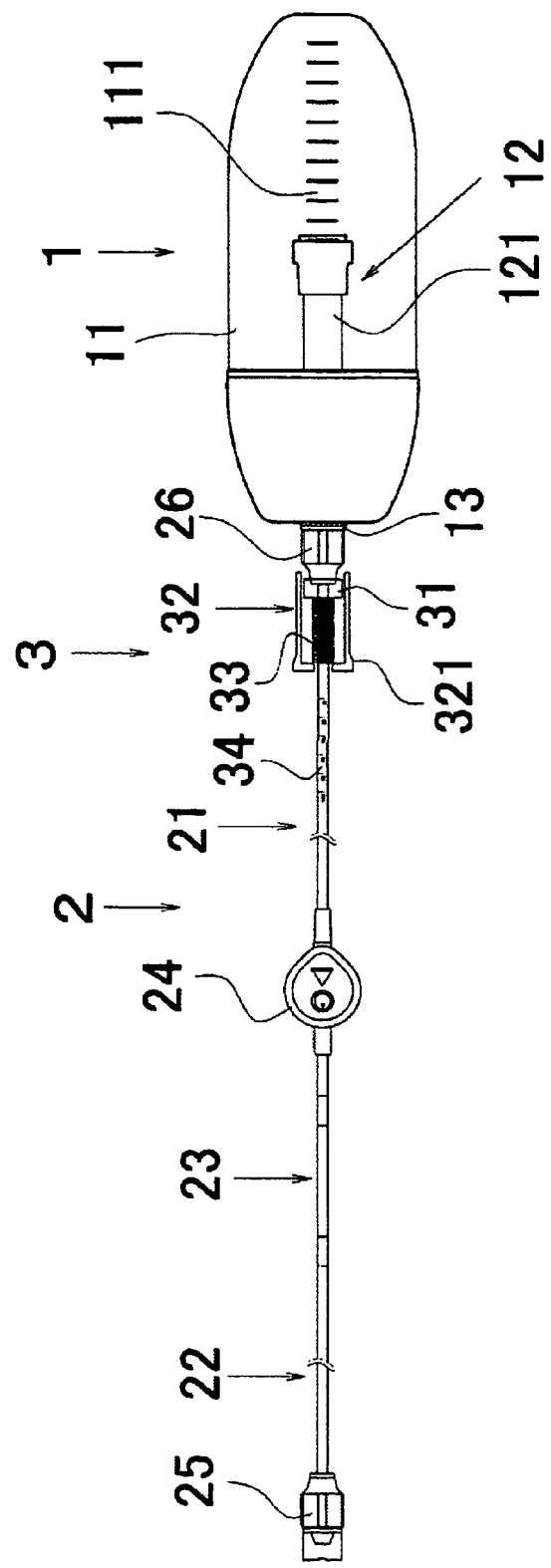
FIG. 1 is an overall view illustrating one embodiment of a drug solution injector with a weighing scale according to the present invention.

1: housing
11: drug solution reservoir
111: scale
12: connecting port
121: balloon made of an elastic body
2: injection line
21: upstream (tube)
22: downstream (tube)
23: flow controller
24: air vent filter
25: connector
26: line proximal end
3: weighing scale
31: body-fixing member
32: holding portion
321: flange
33: spring
34: scale

BEST MODE FOR CARRYING OUT THE INVENTION

A drug solution injector according to the present invention comprises a drug solution reservoir, which is capable of storing a drug solution and then continually discharging a reserved drug solution to the exterior, and an injection line, which is composed of an injection tube for injecting the discharged drug solution into the body, while the drug solution injector is provided with a weighing scale for weighing the drug solution in the drug solution reservoir. In order to protect the drug solution reservoir, it is preferred for the drug solution injector according to the present invention to provide a housing for housing the drug solution reservoir.

The drug solution reservoir used in the present invention is a chamber for holding a drug solution and has a pressurization mechanism for discharging the drug solution from the chamber to the exterior. An outer wall of the drug solution-reserving chamber is provided with at least one hole, which forms a communication between the interior and the exterior of the chamber, through which the drug solution is charged into the chamber and the reserved drug solution is discharged from the drug solution reservoir to the exterior. As the drug solution reservoir, there may be used any one of reservoirs used in conventionally known drug infusion instruments. It is, however, preferred to use a balloon made of an elastic body which can discharge its content by its own deflation (contraction force). As a material for such a balloon include, there may be used any material which is large in elasticity, produces an internal pressure required for discharge of the liquid, and is available for medical use. Examples of preferred materials include, without being limited to, natural rubber, synthetic rubber, elastomer and the like. It is preferred that an inner wall of the balloon is covered with a drug-resistant material which is unchanged in quantity by the drug solution charged in the balloon.

The injection line used in the present invention is a hollow guide tube for injecting the drug solution from the drug solution reservoir to the body. Although it is preferred to use synthetic resins, there is no limit on a material for injection line, provided that it is a material used for drug solution lines, which is available for general medical use. Further, there is no limit on both internal diameter and external diameter of the injection line, but it is general practice to use injection lines that have an internal diameter ranging from about 0.1 to 3.0 mm and an external diameter ranging from about 2.0 to 4.0 mm. Generally, the injection line is directly or indirectly connected at one end to an injection needle for injecting the drug solution into the patient and at the other end to the drug solution reservoir. One end of the injection line to be connected to the injection needle may be provided with a connector for connection to the injection needle, while the other end of the injection line to be connected to the drug solution reservoir may be provided with a connector for connection to the drug solution reservoir. The injection line may be provided at its intermediate portion with a flow controller, air vent filter or a clamp as occasion demands.

There is no limit on the shape and size on the housing which encloses the drug solution reservoir. However, from the standpoint of saving of a storage space, it is preferred to determine the shape and size of the housing such that the housing has a minimum internal space required for housing the drug solution reservoir that is filled with a maximum dosage of the drug solution. A wall of the housing, which forms an internal space of the housing, is provided with at least one port corresponding to the hole of the drug solution reservoir (hereinafter referred to as "connecting port") to allow the interior of the drug solution reservoir to communicate with the exterior of the housing. In case that the housing is provided with one connecting port, it is preferred to design the injection line to be removable from the drug solution reservoir. If the injection line is provided at its lateral portion with a port for filling of the drug solution, the injection line is not required to be of a removable type. In use, after the drug solution reservoir is filled with the drug solution by means of a syringe through the connecting port, the housing is generally connected with the injection line. In case that the housing is provided with two or more connecting ports, the injection line may be of a removable type or of a fixed type.

As a material for the housing, there may be used any materials without limitation, provided that the housing can protect the drug solution reservoir from pressures and shocks applied from the exterior. However, it is preferred to use a transparent or semi-transparent material that allows the user to observe the interior of the housing, more preferably, synthetic resins.

The weighing scale in the present invention may be any devices that can measure the weight of the drug solution in the drug solution reservoir. The scale is fixed to the drug solution reservoir. Preferably, the weighing scale is a device that has an elastic body fixed at one end to the drug solution reservoir or a coupling part of the drug solution reservoir and measures the displacement of the elastic body to determine the weight the weight of the drug solution in the drug solution reservoir.

The weighing scale and the elastic body may be connected with the drug solution reservoir directly or indirectly by means of the connector, injection line or housing.

As an elastic body, there may be used any elastic members. Examples of the elastic members include, but are not limited to, springs and rubbers. Preferred elastic members are springs, more preferably, coil springs. The coil spring is a spring composed of a helically wound metal wire and being extensible in the axial direction of the coil. Although there is no limit on the coil diameter of the spring, it is preferred to set the coil diameter of the spring to a diameter which is greater than the outer diameter of the injection line but does not disturb the handling other than measurement of the weight.

The elastic constant of the elastic body (e.g., spring constant when the elastic body is a spring) may be determined according to the capacity and scale length of the drug solution reservoir to be determined.

The elastic body is preferably arranged so as to be extensible in the direction substantially parallel to the axial direction of the injection line. In case the elastic body is a coil spring, the elastic body is preferably fitted on the drug solution reservoir, housing or injection line so that the injection line is passed through the interior of the coil spring.

The above injection line is preferably marked with a scale that functions as a part of the weighing scale, to show the expansion and contraction of the elastic body according to the weight of the drug solution in the drug solution reservoir. When using the drug solution injector including such a calibrated injection line, the measurement of weight can be carried out by a simple method that involves the steps of picking up the drug solution injector with the injection line being extended upward, holding the holding portion provided on one end of the elastic body, releasing the hand from the injection line to allow the elastic body to be subjected to the weight of the drug solution reservoir and the drug solution contained therein, and reading the scale on the injection line. In order to make the reading of the scale easy, a part of the injection line, which includes a part to which the elastic body is fixed and a calibrated part of the injection line, may be made of a cylindrical member of a nonflexible material with a uniform outer diameter and a straight axis or may be reinforced by a cylindrical member of a nonflexible material with a uniform outer diameter and a straight axis.

The scale provided on the injection line is so calibrated after deduction the weights of the drug solution reservoir and the injection line as to allow the user to determine only the weight of the drug solution in the drug solution reservoir. The scale length provided on the injection line may be set to any value without limitation, but is preferably set to about 5 to 15 cm for measurement of the full weight of the drug solution reservoir. In case the whole length of the scale provided on the injection line is less than about 5 cm, the scale resolution becomes narrow and thus there is a fear of causing inaccuracy of the measurement resulting from increase in error of measurement by visual observation. In case the whole length of the scale exceeds about 15 cm, it becomes an obstruction to the measurement.

The elastic body is generally provided with a holding portion at the other end opposite to one end fixed to the drug solution reservoir, housing or injection line.

The holding portion is connected to a part of the elastic body but is unconnected with the housing, injection line or other part of the injector. The holding portion is so designed as to make it possible to determine decreased capacity of the drug solution in the drug solution injector by holding the holding portion.

The holding portion as well as the body fixing member is composed of two pieces with the same construction or one piece with a hinge and is fixed to the elastic body by press-fitting, bonding or other fixing means. The holding portion is preferably formed into an easily graspable shape with a size The holding portion is preferably formed into a shape and size easily graspable in the fingers and provided with a concavo-convex surface or a flange to be caught in the fingers.

The invention will be described below in detail with reference to embodiments of the present invention, but the present invention is not limited to these embodiments.

Embodiment 1

A drug solution injector of the present invention is illustrated in FIG. 1.

A drug solution injector body 1 comprises a housing 11 and a drug solution reservoir 12. The housing 11 is made of a synthetic resin and is transparent except a part of the housing on the side of an injection line 2 to allow the user to observe an interior of the housing. The housing 11 is marked with a scale 111 as a measure of an injection volume of the drug solution, which is used to know a rough injection volume of the drug solution. The housing 11 is provided at the upper part thereof with a connecting port 13 for connection to the injection line 2. In this embodiment, the housing 11 is provided with one connecting port 13, but it may be provided with two or more connecting ports. In case of one connecting port 13, the injection line 2 is made into a removable type and is connected to the connecting port 13 after injection of a drug solution through a syringe or the like.

Figure 3:
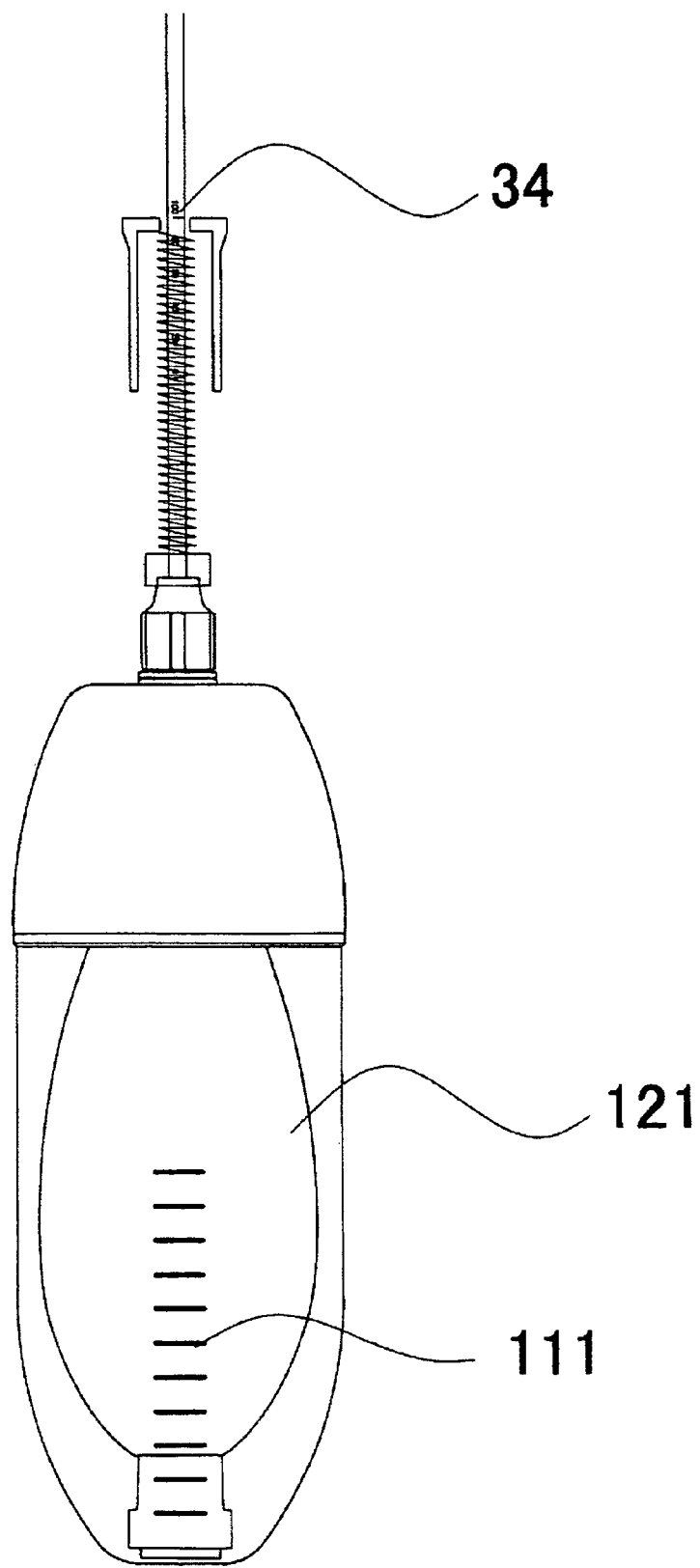
FIG. 3 is an illustration showing the usage state of the weighing scale at the time that the largest amount of a drug solution has been injected into the reservoir.
Figure 4:
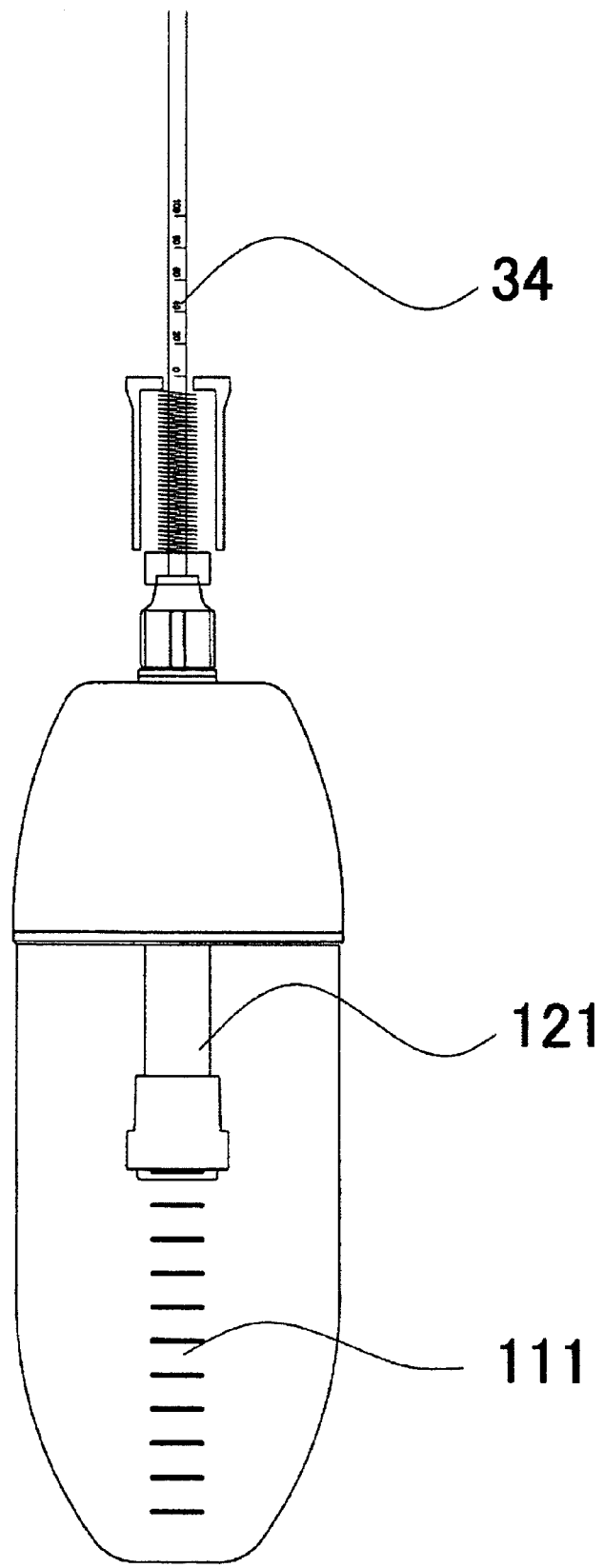
FIG. 4 is an illustration of showing the usage state of the weighing scale after spending all the drug solution in the reservoir.

The drug solution reservoir 12 is composed of a balloon 121 of an elastic body and arranged in the interior of the housing 1. The drug solution reservoir 12 reserves the drug solution in the interior until being expanded to a condition shown in FIG. 3, and then pressurizes the drug solution by deflation of the balloon to release the drug solution to the exterior. When completely discharging the drug solution from the drug solution reservoir 12, the balloon 121 falls into a condition as shown in FIG. 4 and deflates completely.

The injection line 2 is a line used for injection of a drug solution into the body of a patient, and includes an upstream part 21 for connection to the drug solution reservoir and a downstream part 22 for connection to the patient. In case of one connecting port 13, the injection line 2 is of a removable type.

The injection line 2 includes an upstream tube 21, a downstream tube 22, a flow controller 23 arranged between both tubes and an air vent filter 24. The injection line 2 may be further provided with a clamp (not shown in the drawings) in case of necessity. A connector 25 for injection into the patient is attached to a distal end of the downstream tube 22.

The weighing scale 3 is composed of a body-fixing member 31, a holding portion 32 and a spring 33. The injection line 2 is marked with a scale 34 corresponding to the weight of the drug solution contained in the drug solution reservoir 12.

The spring-fixing member 31 is composed of a combination of two identical parts of a synthetic resin, which are fixed by bonding together with a connector sandwiched between them, the connector being attached to a proximal end of the injection line 2. The spring 33 is fixed by bonding at one end thereof to the spring-fixing member 31.

Figure 2:
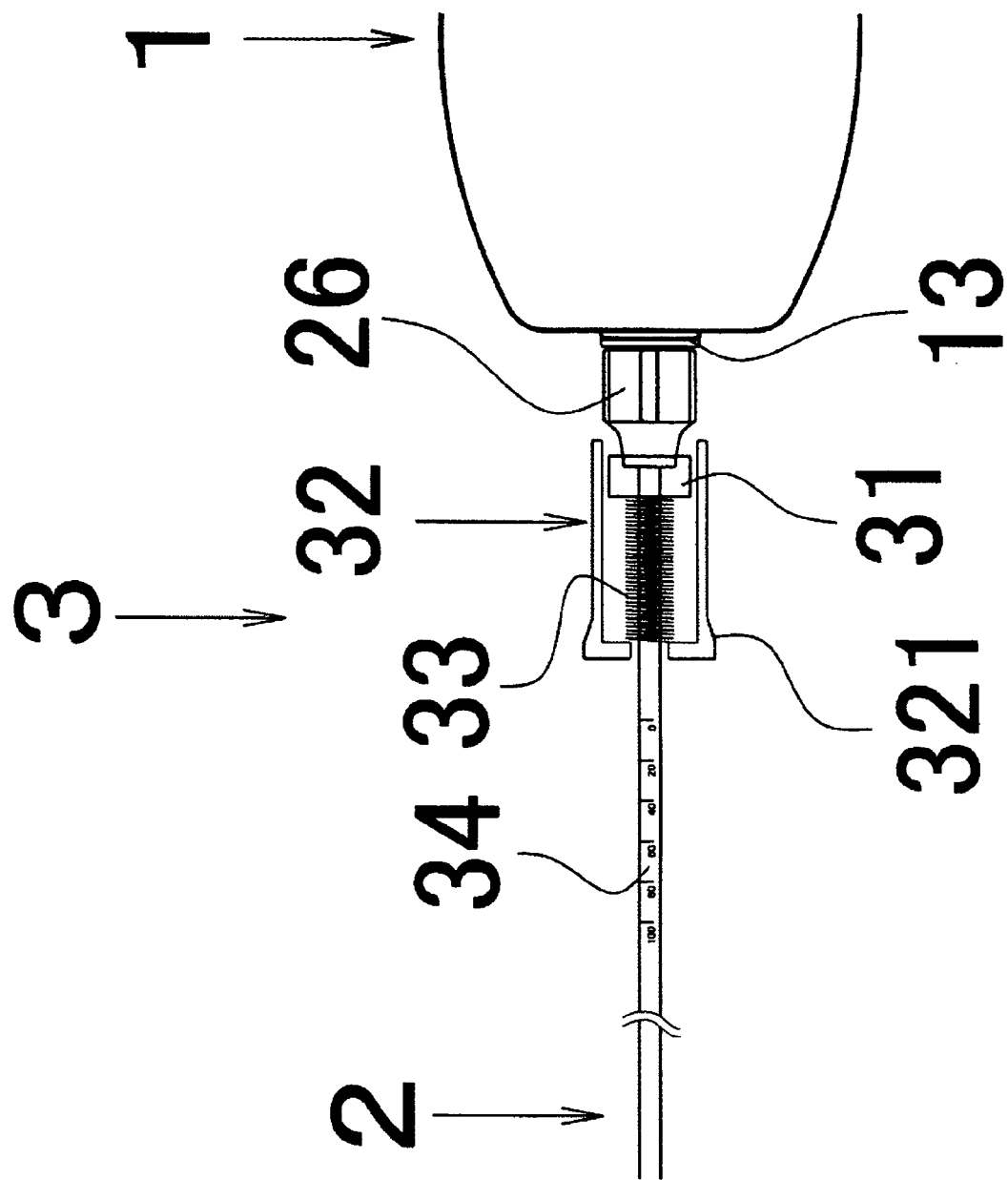
FIG. 2 is an enlarged view of a part of the drug solution injector illustrating a weighing scale in one embodiment of the drug solution injector with a weighing scale according to the present invention.

The holding portion 32 is bonded to the end of the spring 33, but is never fixed to the body 1 and injection line 2. It is possible to determine a decreased amount of the drug solution by picking up the holding portion and then reading the scale 34 (cf. FIGS. 2 and 3). The holding portion 32 is made into a shape and size easily holdable with the fingers, and provided with a flange 321 which is engaged with the fingers at the time of weight measurement.

The spring 33 is a coil spring and is united with the body 1 and the injection line 2 via the injection line 2 being passed through the interior of the spring 33. Calibrated marks 34 on the injection line allow the weight to be read by the length of the spring within the tube.

The injection line 2 are calibrated by marking a point zero 0 for the weight scales 34 under the condition of subtracting the weights of the body 1 and the injection line 2 (refer to calibrated marks 34 in FIG. 4) so as to allow the user to measure only the weight of the drug solution in the drug solution reservoir. A spring constant of the spring 33 is determined according to a capacity of the drug solution reservoir 12 to be used and the length of the scale 34. The diameter of the spring 33 is set to a size which allows the injection line 2 to be inserted into the interior of the spring 33, but which is compact so as not to disturb the user at the time of handling other than measurement of the weight. The length of the scale 34 on the injection line is set to about 5 to 15 cm. The scale length less than 5 cm causes a narrow scale resolution which may cause inaccurate measurement, while the scale length exceeding 15 cm disturbs the weight measurement.

The invention claimed is:

1. A drug solution injector comprising:
    a drug solution reservoir having a chamber for storing a drug solution therein and a pressurization mechanism for continually discharging the stored drug solution to the outside; and
    an injection line connected to the drug solution reservoir to inject the drug solution into the body;
    said drug solution reservoir being secured to a weighing scale for measuring a weight of the drug solution stored in the drug solution reservoir;
    said drug solution injector being manually held with said drug solution reservoir being inverted to extend downwardly from the injection line for enabling the weight of the drug solution stored in the drug solution reservoir to be visually determined by the weighing scale along a predetermined length of the injection line connected to the drug solution reservoir.

2. The drug solution injector according to claim 1, wherein the drug solution reservoir is a balloon composed of an elastic material.

3. The drug solution injector according to claim 1, wherein the weighing scale comprises an elastic body fixed at one end thereof to the drug solution reservoir, said weighing scale measures the displacement of the elastic body to determine the weight of the drug solution contained in the drug solution reservoir.

4. The drug solution injector according to claim 3, wherein the elastic body is extensible in the direction substantially parallel to the axial direction of the injection line.

5. The drug solution injector according to claim 3, wherein the elastic body is a coil spring and wherein the coil spring is arranged so that the injection line passes through the coil of the spring, the spring being fixed at one end thereof to the drug solution reservoir or injection line, said injection line being marked with a scale in the axial direction of the injection line to determine a length of expansion and contraction of the spring.

6. The drug solution injector according to claim 3, wherein the elastic body is provided with a holding portion on the other end opposite to one end fixed to the drug solution reservoir.

7. The drug solution injector according to claim 1, further comprising a housing to protect the drug solution reservoir.

8. A drug solution injector comprising:
    a drug solution reservoir having a chamber for storing a drug solution therein and a pressurization mechanism for continually discharging the stored drug solution to the outside; and
    an injection line connected to the drug solution reservoir to inject the drug solution into the body; and
    a weighing scale including a coil spring fixed at one end thereof to the drug solution reservoir or the injection line, said weighing scale measures the displacement of the coil spring to determine the weight of the drug solution contained in the drug solution reservoir;
    said coil spring being arranged so that the injection line passes through a coil of the coil spring wherein said injection line is marked with a scale in an axial direction of the injection line to determine a length of expansion and contraction of the spring.

9. The drug solution injector according to claim 8, wherein the coil spring is provided with a holding portion on the other end opposite to one end fixed to the drug solution reservoir.

10. The drug solution injector according to claim 8, further comprising a housing to protect the drug solution reservoir.

11. The drug solution injector according to claim 8, wherein the drug solution reservoir is a balloon composed of an elastic material.

12. The drug solution injector according to claim 8, wherein the coil spring is extensible in the direction substantially parallel to the axial direction of the injection line.

* * * * *